United States Patent [19]

Falinower

[11] 4,248,315
[45] Feb. 3, 1981

[54] WEIGHING DEVICE AND INSTALLATION FOR VOLUMETRIC ANALYSIS OF A SAMPLE

[75] Inventor: Charles Falinower, Montelimar, France

[73] Assignee: Ciments Lafarge France, Saint Cloud, France

[21] Appl. No.: 52,680

[22] Filed: Jun. 27, 1979

[30] Foreign Application Priority Data

Jun. 27, 1978 [FR] France ............................. 78 19089

[51] Int. Cl.³ ............................................ G01G 13/14
[52] U.S. Cl. .................................... 177/50; 177/145; 177/165; 422/64; 422/68
[58] Field of Search .................. 177/50, 54, 55, 59, 177/145, 165; 422/62, 64, 68

[56] References Cited

U.S. PATENT DOCUMENTS

| | | | |
|---|---|---|---|
| 2,957,673 | 10/1960 | Brabender | 177/50 |
| 3,502,162 | 3/1970 | Munson | 177/50 |
| 3,870,465 | 3/1975 | Marechal | 422/68 X |

Primary Examiner—Joseph W. Hartary
Attorney, Agent, or Firm—Bernard A. Reiter

[57] ABSTRACT

This invention concerns a weighing device to measure the weight of a sample of powder supplied by a suitable feed-mechanism.

This weighing device comprises at least one sample-holder vessel and a taring vessel, connected to a transfer mechanism which moves the sample-holder vessel from a filling position where it is directly under the feed-mechanism, to receive the sample, to an emptying position, and which also sets the taring vessel and the vessel containing the sample on a weighing mechanism in turn, to measure their weight.

The invention concerns this weighing device and an installation comprising such a device, used in particular for volumetric analysis of a sample of powder, such as raw material for cement-making.

11 Claims, 12 Drawing Figures

WEIGHING DEVICE AND INSTALLATION FOR VOLUMETRIC ANALYSIS OF A SAMPLE

This invention concerns a device for weighing powder, intended more particularly for use with a powder feed-mechanism and a device for chemical analysis of this same powder. This weighing device, combined in this way, can be used in particular for volumetric analysis of raw material to be converted into clinker for cement-making.

This raw material is the homogeneous mixture of limestone and clay burnt in clinker kilns, and it is analysed to find its calcium carbonate content.

Limestone and clay used to feed clinker kilns come from natural sources, and consequently contain a number of impurities, the nature and amount of which vary depending on the origin of the raw materials. Knowledge of the calcium carbonate concentration is needed to ensure regularity in the chemical composition of products entering the clinker kiln.

This invention offers a weighing device which allows fast and accurate measurement of the weight of material to be analysed in the form of a sample of powder taken from a production installation by any suitable means. The volume of this sample is preferably close to a given predetermined figure.

This new weighing device to measure the weight of sample of powder, supplied by a suitable feed-mechanism, is characterized by the fact that it comprises at least one sample-holder vessel and a taring vessel, connected to a transfer mechanism which moves the sample-holder vessel from a filling position where it is directly under the feed-mechanism, to receive the sample, to an emptying position, and which also sets the taring vessel and the vessel containing the sample on a weighing mechanism in turn, to measure their weight.

This weighing device is also characterized by the fact that the transfer mechanism consists of a support which turns on a vertical axle, each vessel being located at the end of an arm carried by a block which turns on a horizontal axle on this support, each vessel being bobbin-shaped, consisting of two truncated cones joined at their smaller ends and surrounded by a ring, the inside diameter of which is between the outside end diameters of truncated cones, and which is fixed to the end of the arm. The other end of the arm supporting the sample-holder vessel can rotate on its axis in the block, and is equipped with a suitable system to make it pivot 180° when in line with the emptying position.

The weighing device preferably comprises a programmer to control rotation of a motor driving the support on its axle and a cam to tip the block downwards, thus lowering each vessel when it is directly above the weighing mechanism and setting it on this mechanism.

This weighing device is particularly suitable for use in an installation for volumetric analysis of a sample of powder, particularly raw material for cement-making.

The following description, illustrated by the accompanying figures, will show other purposes and advantages of the invention, which is in no way confined to this embodiment.

Figure 1:
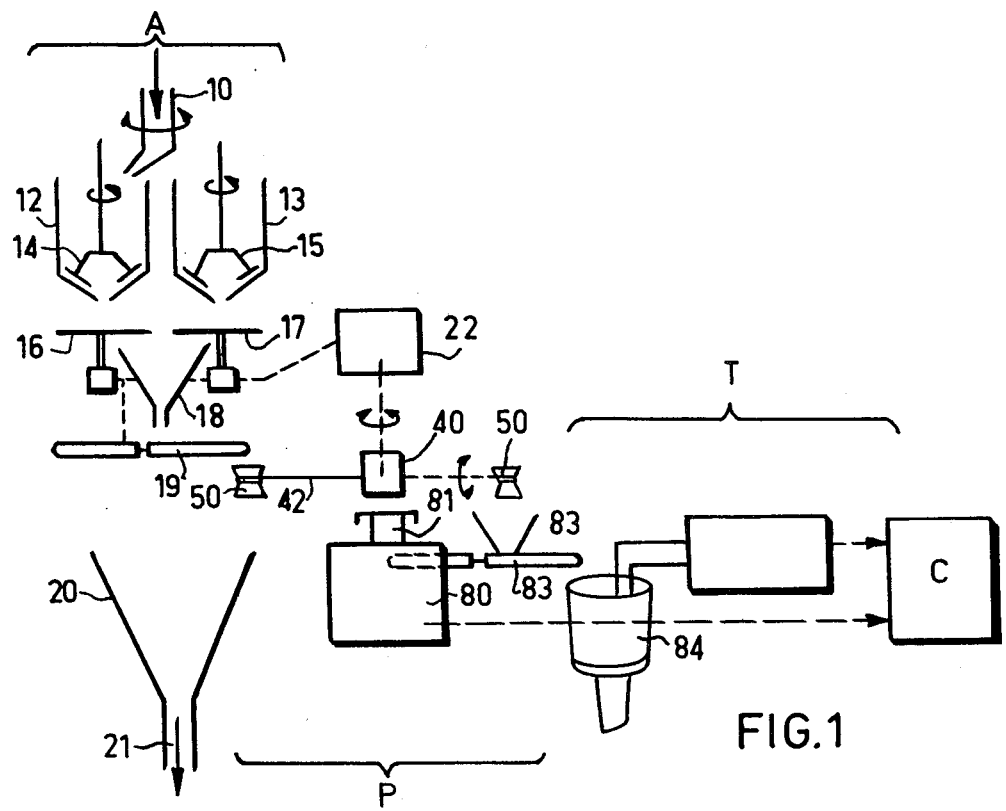
FIG. 1 is a diagrammatical view of an installation for the volumetric analysis of a sample of raw material for cement-making, comprising a feed-mechanism to receive this sample and transfer it to a weighing device, and a device to analyse the sample after weighing, combined with means of computing the calcium carbonate concentration of the sample, on the basis of weighing and analytical data.

The installation shown in FIG. 1, used in this example to measure the calcium carbonate concentration of raw material before conversion into clinker in a cement-works kiln, comprises a feed-mechanism A located above a weighing device P. This mechanism A receives a sample of the raw material for analysis and transfers it to the device P. An analysis device T, below the device P, receives the sample after weighing. The installation also comprises means of computing the calcium carbonate concentration of the sample on the basis of data supplied by the weighing and analysis devices.

The feed-mechanism A comprises a moveable funnel 10 into which material from the sampler (not shown here) is admitted. This funnel 10 dispenses the material into two silos 12 and 13, equipped with shoes 14 and 15, which mix the material and direct it towards the centre of the silo.

Each silo empties on to a revolving tray 16 and 17, controlled by the position of the funnel 10, and a blade (not shown here) on each tray diverts the material and pushes it into a hopper 18, below which is a vibrating chute 19 which transfers it to the device P.

Silos 12 and 13 fill and empty alternately in accordance with a given cycle, lasting 15 minutes, for example.

At the beginning of each cycle, the vibrating chute 19 first vibrates for a certain time, for example one minute, to remove any material still remaining from the previous test. Then, when a new sample of material has been poured out, the chute again begins to vibrate for a fixed, adjustable time, for example 15 to 20 seconds, in order to deliver a given quantity of material, such as 1.5 to 2 g.

Excess material drops into a funnel 20 and through the outlet 21 into a pipe (not shown here).

Figure 2:
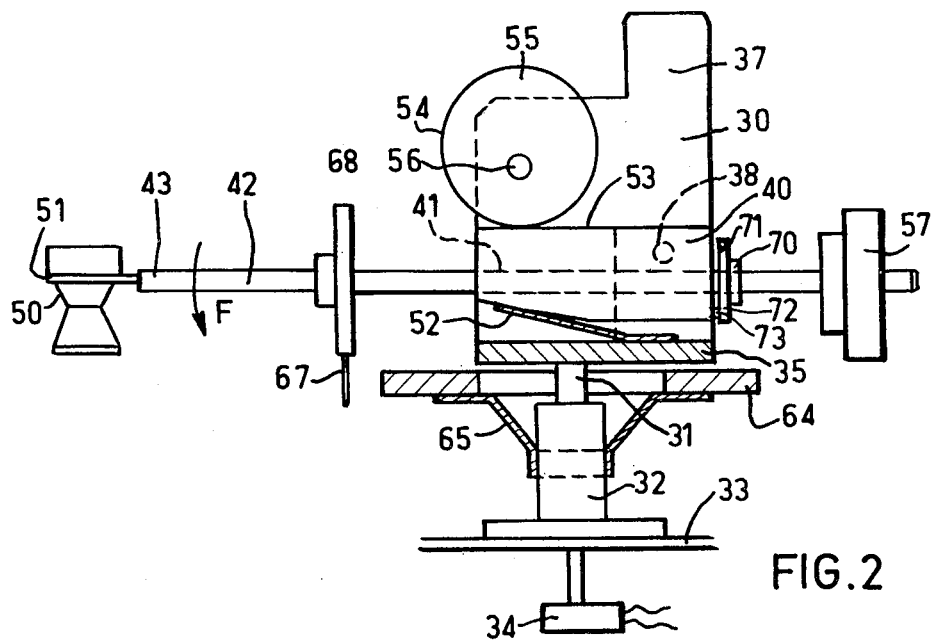
FIG. 2 is a part view in perspective of the weighing device.
Figure 3:
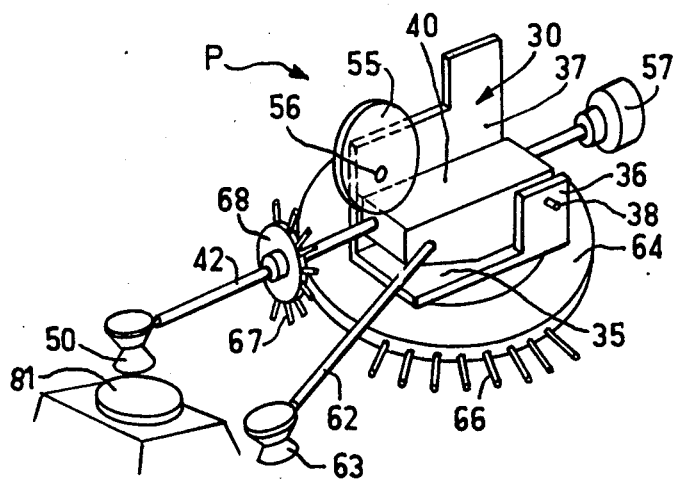
FIG. 3 is a part cross-sectional view of the device in FIG. 2.

All these operations are governed by a programmer 22 accompanying the weighing device P, illustrated in FIGS. 2 and 3.

This device P comprises a support P which turns on a vertical axle 31. This axle revolves in a bearing 32 on a framework 33, and is rotated by a motor 34, of the step-by-step type, for example, controlled by the programmer 22, in accordance with a given cycle described below.

The support 30 comprises a base-plate 35 and two vertical sideplates 36 and 37. Between these is a block 40 which turns on a horizontal axle 38. This block 40 contains a cylindrical boring 41, the centerline of which is perpendicular to the axle 38. A cylindrical shaft 42, both ends of which project beyond the block, fits moveably into this passage. One end 43 of this shaft 42, forming an arm, carries a bobbin-shaped sample-holder vessel 50, consisting basically of two truncated cones joined together at their smaller ends. This vessel is surrounded by a ring 51, the inside diameter of which is between the outside end diameters of the truncated cones, and which is attached to the arm 42.

The arm 42 can therefore rotate on its axis inside the block 40, which itself turns on the axle 38. A spring 52, in this case a flat spring is placed between the base-plate 35 and the block 40, pushing the block upwards, together with the sample-holder vessel 50 and arm 42. This movement is limited by the contact between the top surface 53 of the block 40 and the edge 54 of a cam 55 revolving on an axle 56 fixed to the side-plate 37. In the embodiment illustrated here, the cam is circular, the centre of which is offset from the axle 56. It is rotated on the axle 56 by a motor (not shown here), controlled by the programmer 22. As it revolves, the distance separating the axle 56 from the zone of contact between the cam and the block 40 varies between two extremes, and the smaller of these extremes is such that for the corresponding position of the cam the arm 42 is approximately horizontal, as in FIG. 2.

To prevent abnormal strain on the spring 52, the opposite end of the arm 42 from the vessel 50 carries a counterweight 57.

When the cam 55 rotates into a position such that the distance between the axle 56 and the zone of contact between the cam and the block 40 is greatest, the arm 42 is tipped downwards round the axle 38, in the direction of the arrow F on FIG. 2.

In addition to the arm 42, the block 40 carries a second arm 62, shown in FIG. 3, on the same horizontal plane as the first arm and forming an acute angle with it, of approximately 30°. The end of this arm 62 carries a taring vessel 63, similar to the sample-holder vessel 50, supported like it by a ring similar to the ring 51, and located at the same distance from the axle 31 as the vessel 50.

The weighing device P also comprises an annular disc 64, on the same axis as the axle 31, which it surrounds, slightly below the baseplate 35. It is attached to the bearing 32 by brackets 65, and part of its circumference carries radial pins 66, set at a regular distance apart, and which engage with radial pins 67 on a circular disc 68 fixed to the arm 42 and on the same axis.

When the pins 66 and 67 engage together, which happens for a given angular movement of the support 30 on the axle 31, they cause the arm 42 to rotate on its axis.

As will be described below, beyond a certain point this rotation causes the sample-holder vessel to turn upside down suddenly, in the "emptying" position of the block 40.

A system is provided to position the arm 42 axially in the two positions for which the axis of revolution of the sample-holder vessel 50 is located in the vertical plane containing the arm 42. This system may consist of a disc 70 fitting on to the arm 42, opposite the block 40, and containing 2 hollows 71 and 72, diametrically opposite each other, and both designed to receive an elastic component accompanied by a positioning ball 73 housed in the block 40.

The device P also comprises a balance 80, the pan 81 of which is located on the path of the vessels 50 and 63. When either vessel is directly above this pan, the block 40 tips downwards along the arrow F, as a result of the action of the cam 55. When this happens, the ring holding the vessel is lowered level with the waist of the vessel, thereby releasing it, so that it can be weighed freely.

The device P also comprises a vibrating chute 83, located directly below the vessel 50 when in the emptying position already described. This chute empties into the analysis device 84.

Figure 4:
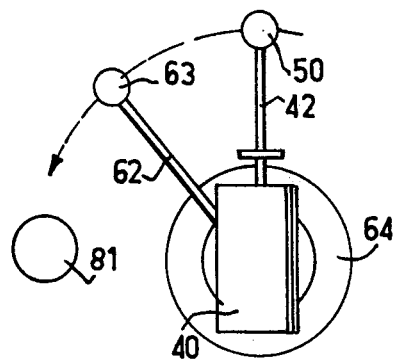
FIGS. 4 to 12 show in diagrammatical form the various stages of operation of this weighing device.
Figure 5:
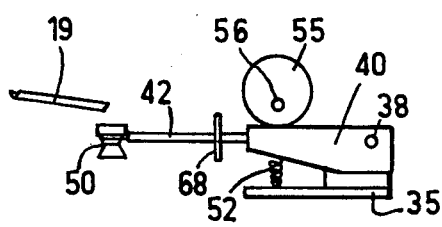

The installation, controlled by the programmer 22, operates as follows. As already mentioned, before the operating cycle begins, the chute 19 is made to vibrate, in order to remove any material from the previous cycle. Then, as this cycle begins, the material for analysis is poured from either silo 12 or 13 into this chute 19 and from there, as a result of vibration of the chute for a given period, into the vessel 50, which is then in the filling position, as shown in FIGS. 4 and 5. If the various positions of the arms holding the vessels 50 and 63 are compared with those of the hour-hand of a clock, the arm 42 when in the filling position is at 12 o'clock, and the arm 62 at approximately 11 o'clock, both arms being horizontal.

Figure 6:
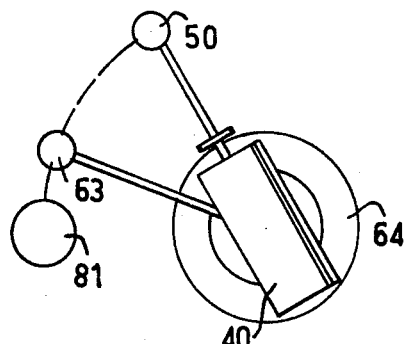

The block 40 then turns, for example in an anticlockwise direction, to a vibration position, as shown in FIG. 6. The arm 42 is then at approximately 11 o'clock. The vessel 50 is subjected to the action of a vibrator (not shown here), in order to make the material settle.

Figure 7:
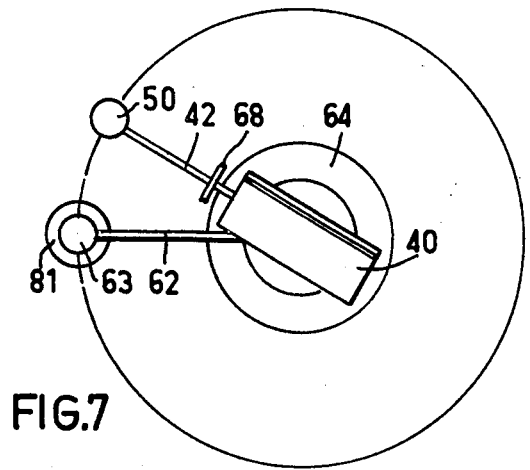
Figure 9:
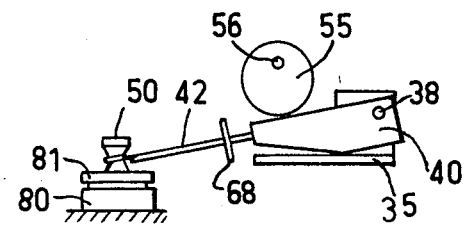

The block 40 continues to rotate, until the vessel 63 is directly above the pan 81 of the balance in the "taring" position, as shown in FIG. 7. It is then at 9o'clock. The block 40 tips downwards as a result of the action of the cam 55, in the same way as shown in FIG. 9 for the vessel 50, and the taring vessel 63 is set on the balance. The weight of this measure 63 is known precisely, and this weighing operation allows any deviation in the balance to be checked and if necessary allowed for.

Figure 8:
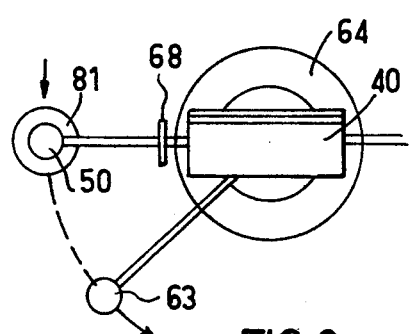

The block is then raised, and continues its movement to a weighing position, as shown in FIGS. 8 and 9, where the vessel 50 is placed in turn on the pan 81 and weighed together with its contents. The weight of the vessel 50 is already known, so that the weight of the contents can be calculated and transmitted to a computer C which stores it.

Figure 10:
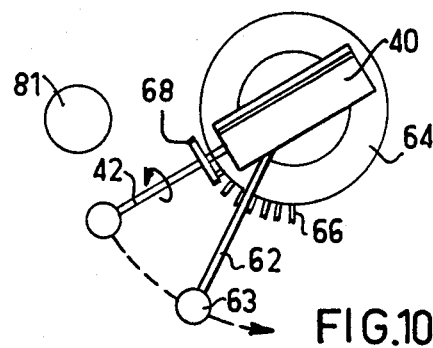
Figure 12:
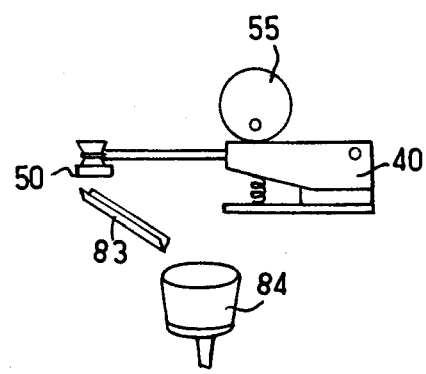
Figure 11:
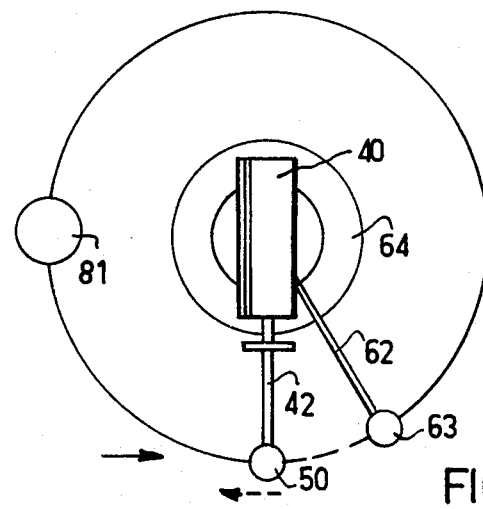

The block 40 is then raised and continues its movement, still in the same direction, with pins 66 and 67 engaging with one another, as shown in FIG. 10. As a result, the arm 42 begins to rotate on its axis. When this rotation goes beyond a certain point, corresponding to the emptying position (this position being at 6 o'clock), the vessel 50 tips up suddenly and empties its contents into the chute 83 and from there into the analysis device P, more specifically a reactor 84, as shown in FIGS. 11 and 12.

The result of the analysis is then transmitted to the computer C which, using the weight of the sample already stored, indicates the calcium carbonate concentration of the raw material.

This result can then be used in any appropriate way in the operation of raw material preparation workshops. The results show the chemical composition of the raw material. On the production line, it will be known between raw material grinders and storage silos, allowing adjustments to be made in the composition of the mixture before entering the kiln. Operation of the kiln is governed by other parameters, such as the quantity of raw material admitted, flow-rate, and free CaO content of the clinker.

From this emptying position, the block 40 begins to rotate in the opposite direction, returning the vessels to their original positions. During the start of this movement, the vessel 50 again turns over, through the engagement of the pins 66 and 67. Just before the vessels reach their original positions, the chute 19 begins vibrating briefly, to remove excess material.

During the return movement, the emptied vessel 50 may stop in the weighing position, to check whether any material remains in it.

At the end of the cycle, the device is ready for the start of a further cycle.

All phases of the cycle are controlled by the programmer 22, which may be a card programmer.

The same programmer is preferably used for automatic control of the analysis done in the device T. This device may be similar to the one described in French patent application N° 78 19 090 dated June 27, 1978.

Naturally, many variants on the weighing device as described here are possible, and it may be applied to other fields than cement works. Suitable calcareous materials are preferably limestone, chalk, marl, seashell, etc. while clay materials may consists of clay, schist, etc. A natural mixture of limestone and clay, known as "cement stone", which merely needs to be fired, may also be used.

What is claimed is:

1. A weighing device to measure the weight of a sample of powder, supplied by a suitable feed-mechanism, characterized by the fact that it comprises at least one sample-holder vessel and a taring vessel, connected to a transfer mechanism which moves the sample-holder vessel from a filling position where it is directly under the feed-mechanism to receive the sample, to an emptying position, and which also sets the taring vessel and the vessel containing the sample on a weighing mechanism in turn, to measure their weight.

2. A weighing device as defined in claim 1, on which the weighing mechanism is characterized by the fact that the transfer mechanism consists of a support on a vertical axle, each vessel being located at the end of an arm carried by a block which turns a horizontal axle on this support, each vessel being bobbin-shaped, consisting of two truncated cones joined at their smaller ends and surrounded by a ring, the inside diameter of which is between the outside end diameters of the truncated cones, and which is fixed to the end of the arm.

3. A weighing device to measure the weight of a sample of powder supplied by a suitable feed-mechanism, characterized by the fact that it comprises at least one sample-holder vessel and taring vessel, connected to a transfer mechanism which moves the sample-holder vessel from a filling position in which it is directly under the feed-mechanism to receive the sample, to an emptying position, and which also sets the taring vessel and the vessel containing the sample on a weighing mechanism in turn, to measure their weight, this transfer mechanism comprising a support which turns on a vertical axle, each vessel being located at the end of an arm carried by a block which turns on a horizontal axle on this support, each vessel being bobbin-shaped consisting of two truncated cones joined at their smaller ends and surrounded by a ring, the inside diameter of which is between the outside end diameters of the truncated cones, and which is fixed to the end of the arm.

4. A weighing device as defined in claims 2 or 3, in which the other end of the arm supporting the sample-holder vessel can rotate on its axis in the block, and is equipped with a suitable system to make it pivot 180° when in line with the emptying position.

5. A weighing device as defined in claim 2 or 3, in which this pivoting device comprises radial pins on a disc fixed to the arm which engage with radial pins on a fixed annular disc surrounding the vertical axle of the support.

6. A weighing device as defined in claims 2 or 3 in which the block is pressed upwards by a spring attached to the support, against an eccentric circular cam, rotation of which moves the block downwards against the spring, thus lowering the arms ans the vessels.

7. A weighing device as defined in claim 6, comprising a programmer designed to control rotation of a motor driving the support on its axle and the cam to tip the block downwards, lowering each vessel when it is directly above the weighing mechanism and setting on this mechanism.

8. A weighing device as defined in claims 1 or 3, comprising a vibration mechanism to vibrate the sample-holder vessel between filling and weighing.

9. An installation for volumetric analysis of a sample of powder, in which a weighing device as defined in claims 1 or 3 is combined with an analysis device into which the sample emptied out by the sample-holder vessel is admitted, this installation comprising a computer which uses data supplied by the weighing and analysis mechanisms to indicate the concentration of the sample.

10. An installation as defined in claim 9, used for volumetric analysis of raw material for cement-making, the concentration measurement being used to operate raw material preparation workshops.

11. An installation as defined in claim 10, in which the feed-mechanism supplying the sample comprises two silos fed alternately by a rotary funnel leading from a sampler device, these silos emptying alternately, through a vibrating chute, into the sample-holder vessel, in the filling position.

* * * * *